United States Patent

Saltz

[11] 4,076,425
[45] Feb. 28, 1978

[54] OPACITY MEASURING APPARATUS

[76] Inventor: Julian Saltz, 16 Benford Drive, Princeton Junction, N.J. 08550

[21] Appl. No.: 658,763

[22] Filed: Feb. 17, 1976

[51] Int. Cl.² .......................................... G01N 21/22
[52] U.S. Cl. .................................. 356/205; 250/575; 356/207
[58] Field of Search .................. 356/93, 95, 205, 207, 356/208; 250/575

[56] References Cited

U.S. PATENT DOCUMENTS

| | | | |
|---|---|---|---|
| 3,684,378 | 8/1972 | Lord | 356/93 |
| 3,743,430 | 7/1973 | Riggs | 356/207 |
| 3,762,817 | 10/1973 | Harklau | 356/205 |
| 3,838,925 | 10/1974 | Marks | 356/207 |
| 3,982,130 | 9/1976 | Trumble | 356/205 |

Primary Examiner—Vincent P. McGraw
Attorney, Agent, or Firm—Martin Sachs

[57] ABSTRACT

An opacity measuring apparatus and method for monitoring the density of effluent flowing through a furnace stack includes a collimated light source directed in a first light path through the stack and the effluent flowing therein, which impinges upon a photoelectric detector providing a first electrical signal related thereto. A second light path, provided by a light pipe disposed in a path external to the stack, directs the light to the photoelectric detector which provides a second electrical signal related thereto. Circuit means provide a third electrical signal related to the ratio of the first electrical signal to the second electrical signal. Also included is an electrical correction signal related to the drift of the electronic circuitry and unwanted contamination occurring in the first light path which is subtracted from the first and second electrical signals prior to obtaining their ratio and circuitry to display and automatically calibrate the apparatus over relatively long periods of time.

13 Claims, 5 Drawing Figures

OPACITY MEASURING APPARATUS

BACKGROUND OF THE DISCLOSURE

The present invention relates to opacity measuring devices and, in particular, to an opacity measuring apparatus and method of obtaining an accurate density (opacity) measurement of the effluent flowing through a furnace stack over relatively long periods of time.

Many systems found in the prior art are designed to measure the density of effluent emanating from furnance stacks. This measurement has become increasingly important of late, since the general public, as well as, environmentalists are concerned with pollution of the atmosphere by waste products obtained by various chemical and sundry product manufacturing processes. These waste products or effluents are frequently expelled via a furnace stack into the atmosphere to be dispersed by air currents. However, the effluents frequently linger on in one place contaminating the air, thereby causing a health hazard to all living things.

The prior art systems of which I am aware approach the problem of obtaining accurate density measurements of effluents emanating from furnace stacks in many ways; each striving to obtain accurate measurements with a simple system requiring a minimum of time and expense for their adjustment and calibration. These systems frequently use a reflective system in which both a measuring light flux, reflected from a reflex-reflector or mirror at the end of a measuring distance and a reference light flux from the original light source are directed onto a photoelectric detector, as disclosed in U.S. Pat. Nos. 3,857,641 to Gass and 3,796,887 to Vincent et al. Other systems utilize a pair of photocells (photoelectric detectors) to accomplish a similar result, as disclosed in U.S. Pat. Nos. 3,838,925 to Marks; 3,743,430 to Riggs and 3,690,774 to Kottle et al. Still another system for measuring the opacity of an effluent utilizes a pair of light sources for this measurement, as disclosed in U.S. Pat. Nos. 3,850,529 to Brugger. Some of the above identified patents, in addition, utilize a light pipe to provide an alternate light path for the collimated light source which is used as a measurement reference. However, to the best of my knowledge, none of the systems disclosed to date, have been able to meet all the requirements of the Environmental Protection Agency for Emission Monitoring as set forth in Part V of the Federal Register, dated Monday, Oct. 6, 1975.

The instant invention overcomes the shortcomings found in the prior art by providing an opacity measuring apparatus which utilizes a single collimated light source, a single photoelectric detector, a light pipe external to the stack providing alternative light paths to yield a reference signal and a correction signal for the output signal, which maintains the required accuracy.

Therefore, it is an object of the present invention to provide a relatively inexpensive accurate apparatus to measure the opacity of effluents flowing through furnace stacks.

Another object of the present invention is to provide an opacity measuring apparatus which is capable of being automatically and continuously calibrated.

A further object of the present invention is to provide an opacity measuring apparatus which may be easily installed and aligned with minimum time and effort.

A still further object of the present invention is to provide an opacity measuring apparatus which is capable of meeting all the requirements set forth by the Environmental Protection Agency.

Another object of the present invention is to provide an apparatus which requires minimum maintenance, and when required, may be readily performed.

SUMMARY OF THE INVENTION

An opacity measuring apparatus for measuring the density of effluent flowing through a furnace stack, according to the principles of the present invention, comprises a collimated light source disposed to direct a narrow beam of light in a first light path within the stack and through the effluent therein, a photoelectric detector disposed to measure the light transmitted across the stack for providing a first electrical signal related thereto, means for providing a second light path for the collimated beam external to the stack, the second light path directing the narrow beam of light towards the photoelectric detector for providing a second electrical signal related thereto, and circuit means coupled to the photoelectric detector for providing a third electrical signal related to the ratio of the first electrical signal to the second electrical signal.

The method of measuring the opacity of an effluent flowing through a furnace stack, according to the principles of the present invention, comprises providing a collimated light source on one side of the stack directed in a first light path within the stack and through the effluent, providing a photoelectric detector on the opposite side of said stack disposed to measure the light transmitted thereto, providing a second light path external to the stack by means of a light pipe for directing the light towards the photoelectric detector, generating first and second electrical signals related to the light received by the photoelectric detector, generating by circuit means a third electrical signal which is related to the ratio of the first electrical signal to the second electrical signal.

The subject matter which I regard as my invention is particularly pointed out and distinctly claimed in the concluding portions of this specification. My invention, itself, however, both as to its organization and method of operation, together with further objects and advantages thereof may best be understood by reference to the following description taken in conjunction with the accompanying drawing.

DESCRIPTION OF THE PREFERRED EMBODIMENT

Figure 1:
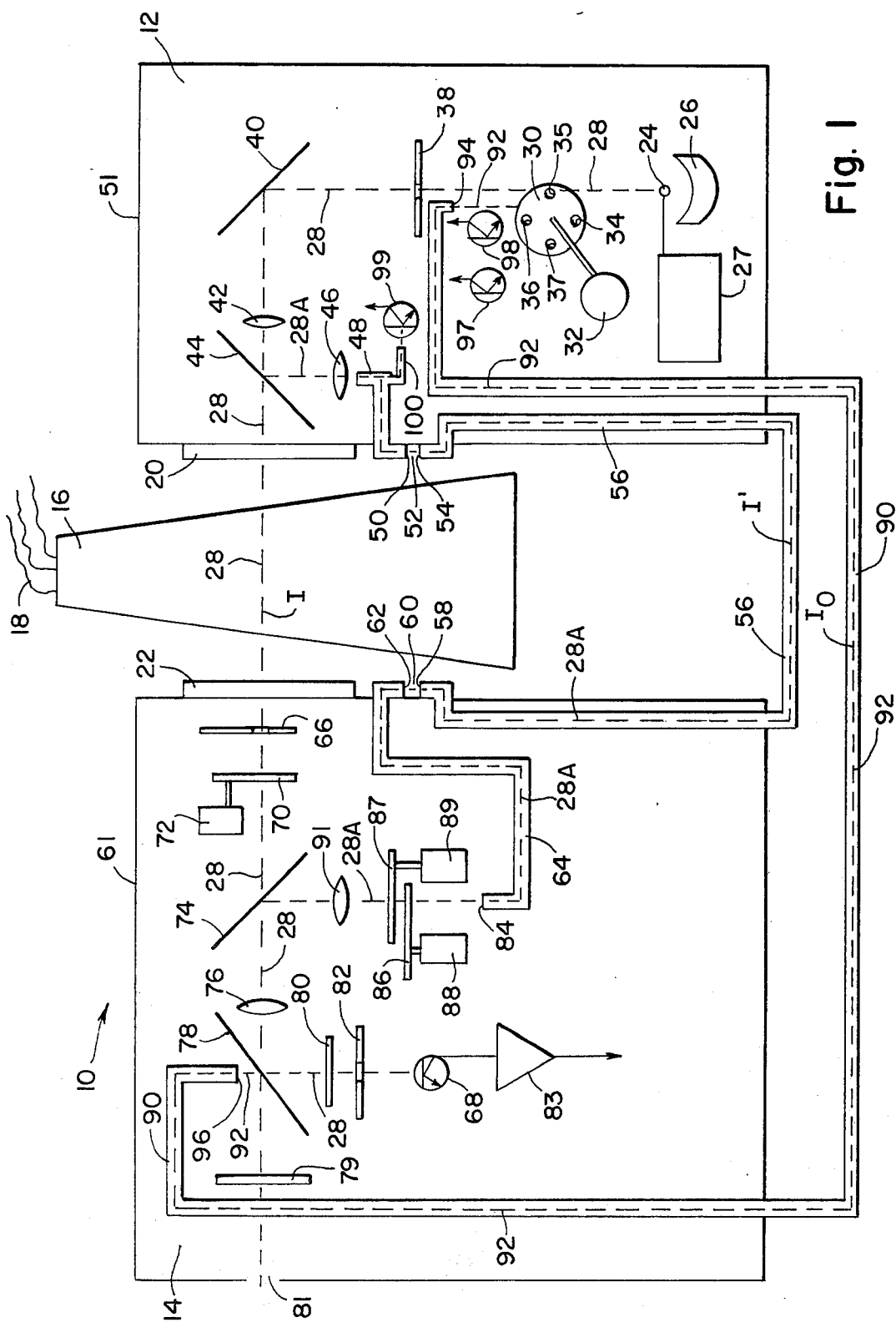
FIG. 1 is a pictorial representation of an opacity measuring apparatus incorporating the principles of the present invention.

Referring now to the drawing, and in particular, to FIG. 1 which is a pictorial representation of a preferred embodiment of an opacity monitoring apparatus 10 incorporating the principles of the present invention. The apparatus 10, may be conveniently separated for explanatory purposes into a transmitting portion 12 and a receiving portion 14 which are adapted to be mounted on opposite sides of a furnace stack 16 through which the effluent 18 flows. The transmitter opening or window 20 is positioned to be in direct alignment with the receiver opening or window 22. The procedure for obtaining the proper alignment of the transmitter window 20 and receiver window 22 will be described hereinafter.

The transmitter window 20 and receiver window are each disposed within a conventional housing which is provided with purging means, not shown, that attempts to insure that foreign materials or particles suspended within the effluent 18 do not deposit thereon and affect the light transmitted therethrough. A stream of gas such as nitrogen or air may be used for this purpose.

A light source 24 is included in the transmitter portion 12. The light source 12 may be obtained from a high intensity lamp preferrably providing photopic light with an approximate wave length peaking at 5500 Angstroms, a laser with a wave length of approximately 6238 Angstroms, or as in the instant embodiment wherein a General Electric lamp #1391 was utilized. The G.E. lamp also includes as an integral part therewith an eliptical reflector 26 which provides a light beam 28 and is energized from a regulated power supply 27. The light beam 28 emanating from light source 24 has placed in its path a chopper timing disc 30 which is coupled to a timing motor 32. The timing disc 30 is provided with circular-shaped apertures 34, 35, 36 and 37 which, in the preferred embodiment, are disposed at ninety degree intervals on the disc 30 to provide the timing signals I, $I_o$ and $I_{DC}$ that control the timing sequence of the opacity measuring apparatus 10 and which will be referred to hereinafter.

The light beam 28, after passing through disc 30 passes through aperture plate 38, is bent 90° by a reflector mirror 40 and enters a collimating lens 42. Upon leaving lens 42 it enters a beam splitter 44 forming an additional light beam 28A which is deflected 90 degrees from the path of light beam 28. Light beam 28 passes through the beam splitter 44, the transmitting window 20, the stack 16 and the effluent 18 flowing therein, and is received by the receiver portion 14 of the opacity measuring apparatus 10, via the receiving window 22, which is disposed diametrically opposite and in line with the transmitting window 20 on the opposite side of the stack 16.

Light beam 28A passes through focusing lens 46 and into a light pipe or fiber optical cable 48. Cable 48 is terminated at one end 50 external to the transmitter housing 51, alongside window 20 and is subjected to the same purging means used on window 20. An air space 52 is provided between light pipe end 50 and the end 54 of light pipe 56 which are in juxtaposition and in alignment. The light beam 28A travels through light pipe 56 to receiving portion 14 in a path, which is external to the stack 16, until its end 58. An air space 60 is provided between end 58 of light pipe 56 and end 62 of light pipe 64, which are in juxtaposition and in alignment. Air space 60 is disposed in close proximity to receiver window 22 external to receiver housing 61 and is subjected to the same purging means used to clear window 22. The purging means is the same as that used for window 20. Light pipes 48, 56, and 64, and air spaces 52 and 60 are, as will be explained hereinafter, used in the measurement of the dust accumulation, the 0%, 50% and span or range calibration and simulates a clear stack. It is to be noted that since air spaces 52 and 60 are in the same environment as windows 20 and 22, respectively, they are subject to the same amount of contamination and particulates deposited thereon. Thus, if the windows 20 and 22 are not cleared by the purging means utilized, neither would air spaces 52 and 60. Therefore, means is provided for determining the amount of contamination appearing on the receiving and transmitting windows.

It is well known by those experienced in the art that reducing the amount of the light beam 28 traveling through windows 20 and 22 appears to the system measurement that the density or opacity of the effluent 18 flowing through the stack 16 has increased, when in fact this has not occurred. This error increases with time and requires that either the system be shut down and the windows cleared, or changed, or some other means be provided for correcting this error. The present invention discloses a means for introducing an electrical correction signal which corrects for drifts in the electronic circuitry and may also be utilized to correct the opacity measurements for the error introduced by the deposition of particulates on the transmitter and receiver windows, thereby maintaining the system accuracy for an extended period of time without requiring shutdown.

Light beam 28 enters receiver window 22 and passes through variable aperture 66 which controls the intensity of light allowed to reach the photoelectric detector 68. The light beam 28 has interposed in its path a shutter 70 which is coupled to and activated by solenoid 72 and reaches beam splitter 74 passing therethrough. The light beam 28 additionally travels through focusing lens 76 and reaches beam splitter 78 where it is deflected 90 degrees, passing through filter 80 and aperture 82 until it impinges upon photoelectric detector 68. The output of photoelectric detector 68 is coupled to an operational amplifier (Op/Amp) 83 which provides an electrical output signal related to the light impinging thereon. The electrical signal is used in the system measurements, as will be explained hereinafter.

Beam splitter 78 also allows a portion of light beam 28 to pass therethrough and impinge upon translucent screen 79 where it may be viewed by looking into viewing aperture 81, thus providing a convenient means for aligning the transmitter window 20 and receiver window 22 with the aperture 66.

The light beam 28A traveling in light pipe 64 leaves the pipe at its other end 84 and has interposed in its path shutters 86 and 87 which are coupled to and activated by solenoids 88 and 89 respectively, and focusing lens 91 before it reaches beam splitter 74. Beam splitter 74 deflects light beam 28A 90° and causes it to follow the same path towards detector 68 as does light beam 28, via lens 76, splitter 78, filter 80, and aperture 82.

The reference signal $I_o$ is obtained by using an additional light path provided by light pipe 90 which permits the light source 24 to couple a light beam 92 to the photo-detector 68 located in the receiving portion 14 in a path external to the stack 16. The chopper timing disc 30 is interposed in the path of light beam 92 as it enters one end 94 of light pipe 90. The beam 92 leaves light pipe 90 at its other end 96 where it passes through beam splitter 78 and follows the path of beam 28 to photoelectric detector 68, via filter 80 and aperture 82.

It is to be noted that although light pipes 56 and 90 have been shown as two separate pipes they may be combined, by those knowledgeable in the art, into a single light bundle which may be designed to provide the two light paths required by the preferred embodiment of the invention.

The timing signals used to control the operating sequence of the solenoids 72, 88, and 89 and the electronic measurement circuitry of the receiving portion 14 are obtained from the light source which provides light beam 28. The electrical timing signals for the electrical reference signal $I_o$ and the electrical correction signal $I_{DC}$ are generated when the light beam 28 travels through apertures 34, 35, 36, and 37 of the disc 30. The beam 28 is interrupted by disc 30 in the proper sequence as it impinges upon photoelectric detectors 97 and 98 located in the transmitting portion 12. The timing for the electrical measurement signal I is obtained when a portion of the light beam 28 is caused to impinge upon photoelectric detector 99, via a light pipe take-off provided in light pipe 48 also located in the transmitting portion 12.

Figure 2:
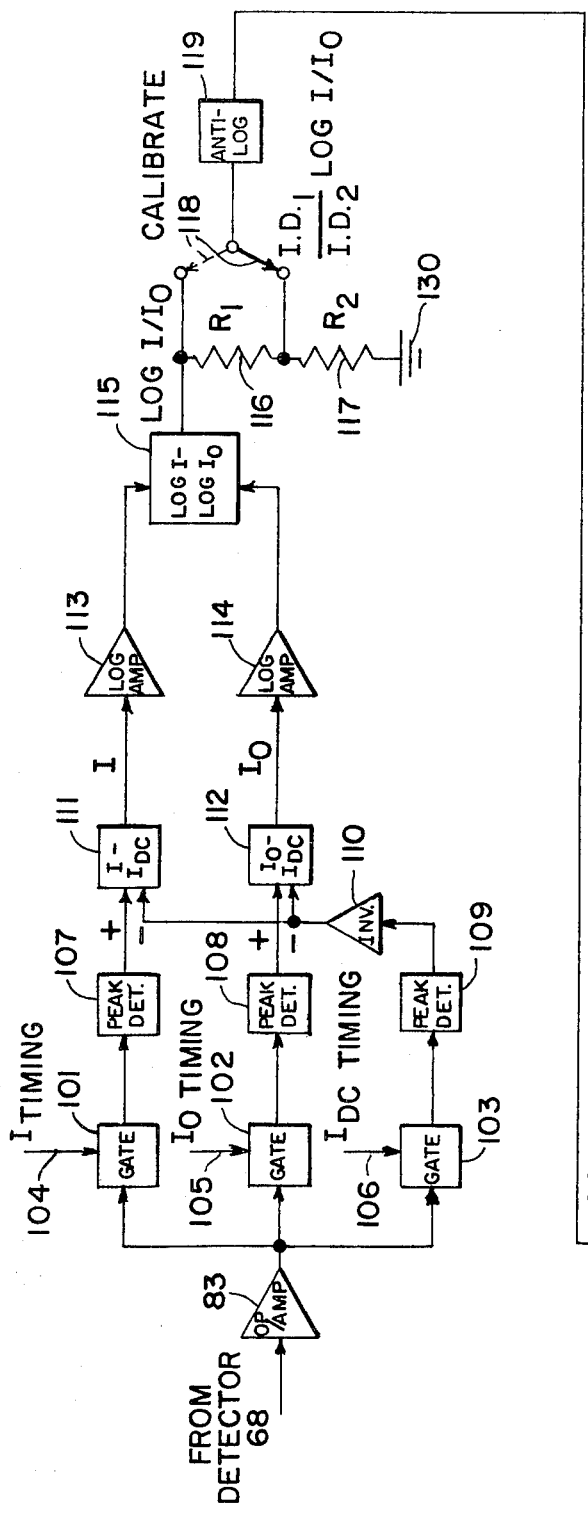
FIG. 2 is a functional block diagram of a preferred embodiment of the light receiving portion of the opacity measuring apparatus.
Figure 2:
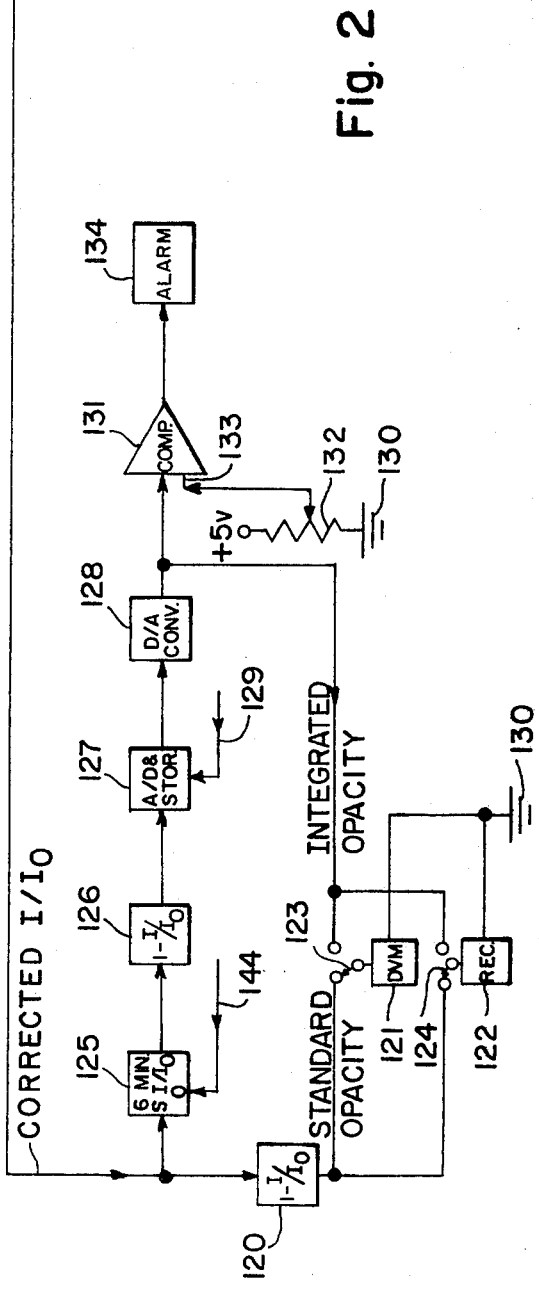
Figure 5:
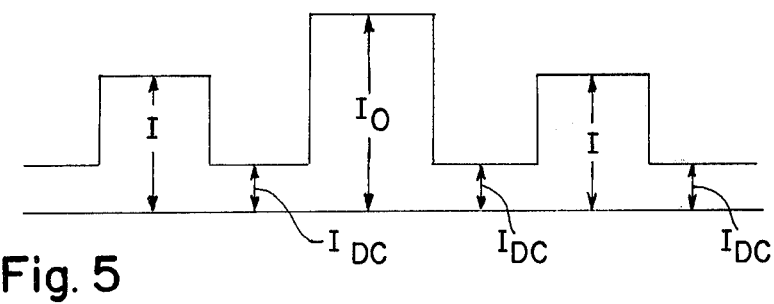
FIG. 5 is a pictorial representation of a typical opacity measurement taken with respect to time.

Refer now to FIG. 2, which shows the functional operation of the opacity measuring apparatus according to the principles of the instant invention. The electrical signals from photoelectric detector 68 are coupled to a field effect operational amplifier (FET Op/Amp) 83 where they are amplified. A typical electrical signal having three different components I, $I_o$ and $I_{DC}$ occurring at different time intervals is shown in FIG. 5. As mentioned earlier, I is the electrical signal obtained from (related to) the light beam which traveled through the furnace stack and effluent; $I_o$ is the electrical signal obtained from (related to) the light beam which traveled through light pipe 90 external to the stack 16, and $I_{DC}$ is the electrical correction signal obtained from (related to) the drift in the electronic measurement circuitry and includes the effect of sunlight, incandescent particulates within the effluent, and photoelectric detector drift. It is to be understood that although one Op/Amp 83 is shown in FIG. 2, any number may be utilized to amplify the electrical signals to the proper level to be handled by the remaining electronic circuitry.

The electrical signals are coupled to analog gates 101, 102 and 103 where the signals are separated into I, $I_o$ and $I_{DC}$, respectively, by their respective timing signals 104, 105 and 106, respectively, being coupled into gates 101, 102 and 103. Each of the signals I, $I_o$ and $I_{DC}$ are then coupled to peak detectors 107, 108 and 109, respectively, where they are peak detected. The output of peak detector 109 is coupled to an inverter Op/Amp 110 where the signal is inverted (made negative). The inverted $I_{DC}$ signal is then coupled to summing Op/Amps 111 and 112 into which are coupled the I and $I_o$ signals from detectors 107 and 108 respectively. Thus, the electrical output signals form Op/Amps 111 and 112 have the $I_{DC}$ (correction) signal removed from them. An additional correction signal related to the dust and particulates appearing on windows 20 and 22 may also be introduced in a manner similar to the introduction of $I_{DC}$ thus continuously correcting the I signal for deposited particulates. The corrected I and $I_o$ electrical signals are coupled to logarithmic Op/Amps 113 and 114, thereby providing at their output a log of the input signals thereto. The output of log Op/Amps 113 and 114 are coupled to subtracting Op/Amp, 115 thus providing at its output a signal related to the log of $I/I_o$. The log $I/I_o$ signal is coupled to a voltage divider network consisting of a resistor 116 ($R_1$) and a resistor 117 ($R_2$) serially coupled to reference ground 130.

The value of the resistor 116 ($R_1$) and the resistor 117 ($R_2$) is determined as follows:

$$R_2 = R_1/(I.D._2/I.D._1 - 1)$$

Figure 3:
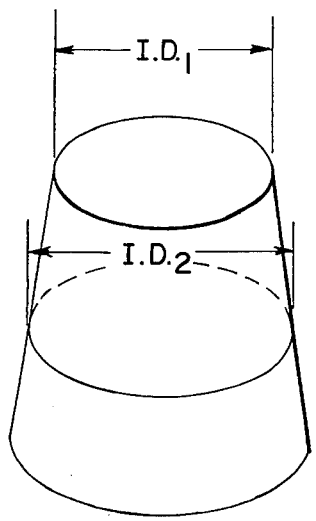
FIG. 3 is a pictorial representation of the measurement compensation technique utilized to compensate for the location of the light transmitter and receiving portion of the opacity measuring apparatus on a typical furnace stack.

Refer to FIG. 3, which shows that $I.D._2$ is the internal diameter of the furnace stack at the position that the opacity measuring apparatus is mounted, and $I.D._1$ is the internal diameter of the furnace stack at its exit orifice. The value of $R_1$ and $R_2$ must be determined for each stack upon which the apparatus is mounted. Thus, by utilizing the electrical signal appearing at the juncture of $R_1$ and $R_2$ in the measurement, the electrical signal is modified to correct for the location of the measuring apparatus, if it is not located at the exit orifice of the furnace stack. The electrical signal (V) then at the juncture of $R_1$ and $R_2$ is:

$$I.D._1/I.D._2 \times \log I/I_o = V;$$

and it or the log $I/I_o$ may be selected by switch 118 for calibration purposes. The selected signal is coupled to anti-log Op/Amp 119 where the output thereof is $I/I_o$ or corrected $I/I_o$. The $I/I_o$ signal is coupled to a subtraction Op/Amp 120 where it is subtracted from unity (1 volt), yielding $1-I/I_o$ at the output thereof which, by definition, is Opacity. This electrical signal representative of (related to) Opacity is coupled to a conventional digital voltmeter (DVM) 121 or recorder 122, via selector switches 123 or 124, respectively.

The $I/I_o$ signal from the anti-log Op/Amp 119 is also coupled to an integrating Op/Amp 125 which integrates for a fixed period of time, and then to a subtracting Op/Amp 126, similar to Op/Amp 120, yielding an output related to $1-I/I_o$. This signal is coupled to an analog to digital (A/D) and storage network 127 where the signal is stored in digital format. The integrating Op/Amp 125 and A/D storage network dumps or releases the stored signal into a digital to analog (D/A) converter 128 when commanded to by a signal pulse coupled thereto, via a line 129. The output signal from the D/A converter 128 is coupled to a conventional DVM 121 or the recorder 122, via selector switches 123 or 124 respectively; the DVM and recorder both have their ground terminals connected to reference ground 130.

The output of the D/A converter 128 may also be coupled to a comparator Op/Amp 131 which has an adjustable voltage obtained from variable resistor 132 coupled to its reference input terminal 133; the value of voltage set is related to the acceptable opacity limit. When the signal coupled to the comparator 131 from D/A converter 128 exceeds the voltage value set by resistor 132 it yields an output voltage which may be coupled to an alarm device providing either a visible or audible indication that the set opacity limit has been exceeded, thus requiring corrective action.

Figure 4:
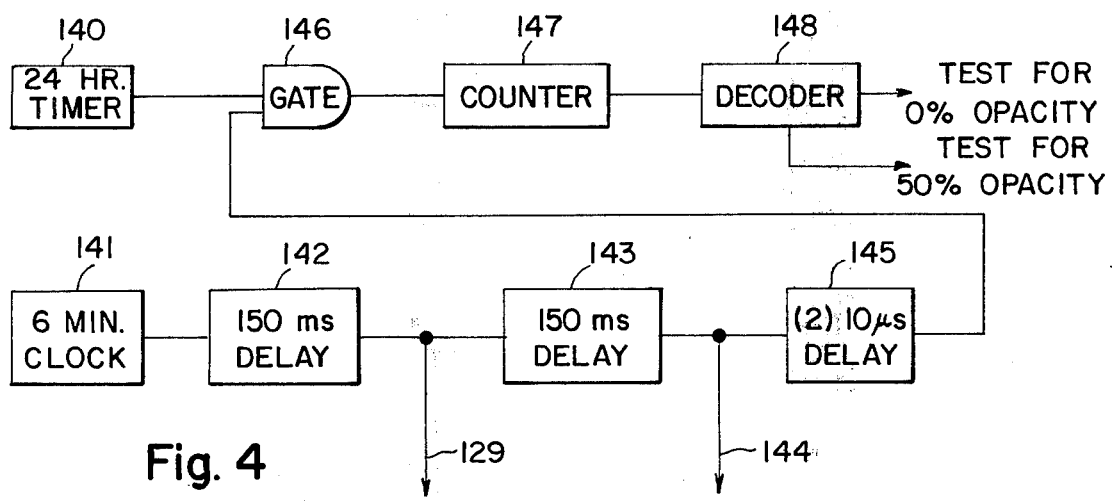
FIG. 4 is a functional block diagram of the timing logic of the preferred embodiment of the opacity measuring apparatus.

The timing sequence of the preferred embodiment is shown in FIG. 4. The 24 hour timer 140 includes a conventional timer motor, cam and microswitch arrangement, not shown, to provide a timing pulse occurring once every 24 hour period. The 6 minute clock 141 is a conventional solid state circuit arrangement, not shown, which provides an output pulse once every 6 minutes. The output pulse from the six minute clock 141 is coupled to a 150 millisecond delay circuit 142. Delay circuit 142 provides an output pulse on line 129 (FIG. 2) which causes the integrator A/D Op/Amp 127 to transfer its voltage to the D/A converter 128 and is also coupled to a second 150 millisecond delay circuit 143 which provides an output pulse to discharge the integrator Op/Amp 125 (FIG. 2), via line 144. The output from delay circuit 143 is also coupled to the 10 microsecond delay circuits 145 that provide an output pulse to gate 146 together with the pulse from the 24 hour timer 140.

The output of gate 146 is coupled to a counter 147 which provides an output pulse to a decoder 148. Decoder 148 in sequence provides a pulse which activates solenoids 72, 88, 89 (FIG. 1) for the 0% and 50% opacity calibration checks.

In operation, the light beam 28 emanating from light source 24 is interrupted by chopper timing disc 30 and passes through apertures 34–37 provided therein. Light pipe cable 90 is 45 degrees from aperture plate 38 in order that the light may enter light pipe 90 and photoelectric detector 97 when the chopper disc 30 rotates 45 degrees from the opening in aperture plate 38, thus providing the timing pulse for the $I_o$ signal. The timing for the $I_{DC}$ signal is obtained by providing the photoelectric detector (photodiode) 98, 45° in the opposite direction from the opening in aperture plate 38. The diameter of the opening in aperture plate 38 and the focal length of lens 42 determine the divergence of the light beam 28.

The beam 28 is reflected by mirror 40 and split by beam splitter 44 so that part of the beam travels through the stack 16 and effluent 18 while the other part travels through light pipe 48, 56, and 64 simulating a clear stack or 0 opacity, which is used once every 24 hour period to calibrate the system. The system is initially adjusted so that the same output is obtained from photoelectric detector 68 when the light travels through light pipe 90 and light pipes 48, 56, and 64 so that any deviation in opacity between the two indicates the amount of dust or particulates that have deposited in the air spaces 52 and 60 and, therefore, on the windows 20 and 22. Thus, when the deviation reaches unacceptable limits the system may be closed down and cleaned.

During normal operation the light pipes 48, 56 and 64 are blocked by shutter 86 which is activated by rotary solenoid 88.

The calibration cycle has two steps; a 100% transmittance (0 opacity) test and a 50% transmittance test or some value that is close to the opacity of the effluent to be measured. The calibration cycle is preferably activated once every 24 hours as noted earlier, but may be activated once each second to provide a continuous correction signal.

In order to check 0 opacity solenoid 88 is activated raising shutter 86 and allowing light to travel through lens 91. Solenoid 72 is activated also, placing shutter 70 in the path of light beam 28, thereby blocking it. The light beam traveling in the light pipe has replaced the beam traveling in the stack and is attenuated only by particulate accumulation occurring in the air spaces 52 and 60 as mentioned earlier. In this mode, the system will measure the ratio of $I'/I_o$.

The second step is similar to the first step, except that solenoid 89 is activated in addition to solenoid 88 and a known neutral density filter such as shutter 87 is placed in the path of light beam 28A. A new ratio $I''/I_o$ is then obtained. Thus, the complete optics and electronics of the system has been checked since the ratio of $I'/I_o$ has initially been set to 1. As dust collects in the air spaces this will reduce to a value less than 1. In the preferred embodiment, the 0 opacity of the first step is maintained for 6 minutes, then the neutral density filter is inserted for 6 minutes. At the end of 12 minutes solenoids 88, 89 and 72 are deactivated and the light beam 28 passing through the stack and effluent is measured.

It is to be noted, that during the calibration cycle the selector switch 118 (FIG. 2) is maintained in the calibrate position utilizing the full output signal from Op/Amp 115. Since the system utilizes a 6 minute clock 141 (FIG. 4) for calibration measurements, it also used the clock pulses to update the I, $I_o$, and $I_{DC}$ signals every six minutes by transferring the signals from the integrators to the A/D converter.

It will be understood that various changes in the details, materials arrangements of parts and operating conditions which have been herein described and illustrated in order to explain the nature of the invention may be made by those skilled in the art within the principles and scope of the instant invention.

Having thus set forth the nature of the invention, what is claimed herein is:

1. An opacity measuring apparatus for measuring the opacity of effluent flowing through a furnace stack comprising:
    (a) a collimated light source disposed to direct a narrow beam of light in a first light path within said stack and through said effluent therein;
    (b) a photoelectric detector disposed to measure the light transmitted across said stack for providing a first electrical signal related thereto;
    (c) means for providing a second light path for the collimated beam external to said stack, said second light path directing said narrow beam of light towards said photoelectric detector for providing a second electrical signal related thereto; said second electrical signal being displaced in time from said first electrical signal;
    (d) circuit means coupled to said photoelectric detector for providing a third electrical signal related to the ratio of said first electrical signal to said second electrical signal; and
    (e) means for peak detecting said first and second electrical signals, said peak detecting means peak detecting said first and second electrical signals prior to obtaining said third electrical signal.

2. An opacity measuring apparatus according to claim 1 further including means for blocking of the light in said first and second light paths and providing an electrical correction signal related to the amount of contamination in said first light path and the unwanted circuit means drift in said first and second light paths and subtracting said correction signal from said first and second electrical signals.

3. An opacity measuring apparatus according to claim 1 for providing an electrical correction signal related to the deposited effluents on the lenses occuring in said first light path and adding said effluent correction signal to said first electrical signal.

4. An opacity measuring apparatus according to claim 1 further including means for displaying said third electrical signal.

5. An opacity measuring apparatus according to claim 4 wherein said display means comprises a voltmeter.

6. An opacity measuring apparatus according to claim 4 wherein said display means comprises a recording device.

7. An opacity measuring apparatus according to claim 3 further including circuit means for correcting said third electrical signal relative to the location of said collimated light source on said stack.

8. An opacity measuring apparatus for measuring the opacity of effluent flowing through a furnace stack comprising:
  (a) a collimated light source disposed to direct a narrow beam of light in a first light path within said stack and through said effluent therein;
  (b) a photoelectric detector disposed to measure the light transmitted across said stack for providing a first electrical signal related thereto;
  (c) means for providing a second light path for said collimated beam external to said stack, said second light path directing said narrow beam of light towards said photoelectric detector for providing a second electrical signal related thereto; said second electrical signal being displaced in time from said first electrical signal;
  (d) circuit means coupled to said photoelectric detector for peak detecting said first and second electrical signals;
  (e) circuit means coupled to said peak detecting circuit means for providing a third electrical signal related to the ratio of said first peak detected electrical signal to said second peak detected electrical signal; and
  (f) display means for displaying said third electrical signal.

9. An opacity measuring apparatus according to claim 8 further including means for blocking the light in said first light path and providing an electrical correction signal related to the unwanted contamination occurring in said first light path and circuit means for subtracting said electrical correction signal from said first and second peak detected electrical signals prior to obtaining said third electrical signal.

10. The method of measuring the opacity of an effluent flowing through a furnace stack comprising:
  (a) providing a collimated light source on one side of said stack directed in a first light path within said stack and through said effluent;
  (b) providing a photoelectric detector on the opposite side of said stack disposed to measure the light transmitted thereto;
  (c) providing a second light path external to said stack by means of a light pipe for directing said light towards said photoelectric detector;
  (d) generating first and second electrical signals related to the light received by said photoelectric detector;
  (e) generating by circuit means, a third electrical signal which is related to the ratio of said first electrical signal to said second electrical signal; and
  (f) peak detecting said first and second electrical signals prior to generating said third electrical signal.

11. The method of measuring the opacity of effluent according to claim 10 further including generating an electrical correction signal related to the amount of unwanted contamination occurring in said first light path and adding said electrical correction signal to said first electrical signal before said third electrical signal is generated.

12. In an opacity measuring apparatus for measuring the opacity of an effluent flowing through a stack having a transmitting portion and a receiving portion including a light beam traveling through said stack, at least one photoelectric detector at the receiving portion, and a first light path from said transmitting portion to said receiving portion external to said stack, the improvement which comprises adding a beam splitter in the transmitting portion disposed in the path of said light beam, a collimating lens disposed to focus one portion of said light beam into a second light path from said transmitting portion to said receiving portion, a second beam splitter disposed in the path of said light beam in said receiving portion adapted to receive said light beam, via a collimating lens from said second light path, and means for selectively interrupting said first and second light paths and inserting in said second light beam path a known neutral density filter for obtaining a "0" and span calibration for said light beam in said first light path.

13. In an opacity measuring apparatus for measuring the opacity of an effluent flowing through a stack having a transmitting portion and a receiving portion including a light beam traveling through said stack, at least one photoelectric detector at the receiving portion, the improvement which comprises adding a beam splitter in the transmitting portion disposed in the path of said light beam, a collimating lens disposed to focus one portion of said light beam into a light path from said transmitting portion to said receiving portion external to said stack, a second beam splitter disposed in the path of said light beam in said receiving portion adapted to receive said light beam via a collimating lens from said external light beam path, and means for selectively interrupting said external and internal light beam paths and inserting in said external light beam path a known neutral density filter for obtaining a "0" and span calibration for said light beam in said first light path.

* * * * *